US011298079B2

(12) United States Patent
Cho et al.

(10) Patent No.: US 11,298,079 B2
(45) Date of Patent: Apr. 12, 2022

(54) SMART SHOE SYSTEM FOR CALCULATING ENERGY EXPENDITURE

(71) Applicant: THE INDUSTRY & ACADEMIC COOPERATION IN CHUNGNAM NATIONAL UNIVERSITY (IAC), Daejeon (KR)

(72) Inventors: Kang Hee Cho, Daejeon (KR); Jong-Hyun Park, Gyeryong-si (KR)

(73) Assignee: THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 84 days.

(21) Appl. No.: 16/635,232

(22) PCT Filed: Jul. 26, 2018

(86) PCT No.: PCT/KR2018/008467
§ 371 (c)(1),
(2) Date: Jan. 30, 2020

(87) PCT Pub. No.: WO2019/027182
PCT Pub. Date: Feb. 7, 2019

(65) Prior Publication Data
US 2020/0367822 A1    Nov. 26, 2020

(30) Foreign Application Priority Data

Jul. 31, 2017   (KR) .................. 10-2017-0096800

(51) Int. Cl.
*A61B 5/00*     (2006.01)
*A61B 5/103*    (2006.01)
(Continued)

(52) U.S. Cl.
CPC .......... *A61B 5/6807* (2013.01); *A61B 5/1038* (2013.01); *A43B 3/34* (2022.01);
(Continued)

(58) Field of Classification Search
CPC . A43B 3/00; A43B 3/0005; A61B 2562/0247; A61B 5/1038; A61B 5/1118;
(Continued)

(56) References Cited

U.S. PATENT DOCUMENTS 5,373,651 A * 12/1994 Wood .................. A43B 3/00
36/1
6,183,425 B1 * 2/2001 Whalen ............... A61B 5/1038
600/592
(Continued)

FOREIGN PATENT DOCUMENTS

CN    105595531 A  *  5/2016
JP    2013503660 A    2/2013
(Continued)

OTHER PUBLICATIONS

PCT International Search Report dated Oct. 24, 2018 for Intl. App. No. PCT/KR2018/008467, from which the instant application is based, 5 pgs.

*Primary Examiner* — May A Abouelela
(74) *Attorney, Agent, or Firm* — Fredrikson & Byron, P.A.

(57) ABSTRACT

A smart shoes system for calculating energy expenditure based on a stance speed which indicates the ratio of the length of smart shoes to the time which is from the moment the smart shoes touch the ground to the moment the shoes come off the ground.

7 Claims, 3 Drawing Sheets

(51) Int. Cl.
*A61B 5/11* (2006.01)
*A43B 3/34* (2022.01)

(52) U.S. Cl.
CPC .............. *A61B 5/112* (2013.01); *A61B 5/1118* (2013.01); *A61B 2562/0247* (2013.01)

(58) Field of Classification Search
CPC ..... A61B 5/112; A61B 5/6807; A61B 5/1123; A61B 5/1036; A61B 5/1114; A61B 5/1122
USPC .................................................. 600/587, 592
See application file for complete search history.

(56) References Cited

U.S. PATENT DOCUMENTS

| | | | | |
|---|---|---|---|---|
| 6,493,652 | B1* | 12/2002 | Ohlenbusch | A61B 5/1038 324/160 |
| 6,876,947 | B1* | 4/2005 | Darley | A61B 5/1118 702/160 |
| 11,016,111 | B1* | 5/2021 | Chuang | A61B 5/112 |
| 2003/0163287 | A1* | 8/2003 | Vock | G01G 19/44 702/187 |
| 2006/0143645 | A1* | 6/2006 | Vock | A61B 5/6833 725/9 |
| 2008/0096726 | A1* | 4/2008 | Riley | G09B 5/02 482/8 |
| 2011/0054359 | A1* | 3/2011 | Sazonov | A61B 5/4866 600/595 |
| 2011/0087445 | A1* | 4/2011 | Sobolewski | A43B 5/00 702/44 |
| 2012/0268592 | A1* | 10/2012 | Aragones | G09B 19/0038 348/143 |
| 2013/0041590 | A1* | 2/2013 | Burich | A61B 5/1118 702/19 |
| 2013/0201036 | A1* | 8/2013 | Stahlin | A43B 3/0005 340/944 |
| 2013/0324368 | A1* | 12/2013 | Aragones | A63B 71/0619 482/8 |
| 2014/0200834 | A1* | 7/2014 | Ross | G01L 25/00 702/41 |
| 2015/0025816 | A1* | 1/2015 | Ross | A43B 17/00 702/44 |
| 2015/0100251 | A1* | 4/2015 | Solinsky | A63B 24/0006 702/33 |
| 2015/0153374 | A1* | 6/2015 | Balakrishnan | G01P 15/00 702/178 |
| 2015/0269866 | A1* | 9/2015 | Ellis | A61B 5/0024 434/127 |
| 2016/0067584 | A1* | 3/2016 | Giedwoyn | A61B 5/112 700/91 |
| 2016/0349076 | A1* | 12/2016 | Campos Gallo | A61B 5/1038 |
| 2017/0188950 | A1* | 7/2017 | Gazdag | A43B 3/0005 |
| 2017/0189752 | A1* | 7/2017 | Mohrman | A61B 5/7271 |
| 2017/0265584 | A1* | 9/2017 | Walker | G01L 5/12 |
| 2017/0268923 | A1* | 9/2017 | Yamada | A61B 5/103 |
| 2018/0028862 | A1* | 2/2018 | Statham | A63B 24/0062 |
| 2018/0206586 | A1* | 7/2018 | Akay | A43B 3/0015 |
| 2018/0279915 | A1* | 10/2018 | Huang | A61B 5/4023 |
| 2018/0333078 | A1* | 11/2018 | Malawey | A43B 3/0005 |
| 2018/0360157 | A1* | 12/2018 | Jeong | A61B 5/6807 |
| 2019/0105217 | A1* | 4/2019 | Prattichizzo | A61H 3/00 |
| 2019/0150796 | A1* | 5/2019 | Fukushi | A61B 5/1036 |

FOREIGN PATENT DOCUMENTS

| | | |
|---|---|---|
| JP | 2014010823 A * | 1/2014 |
| JP | 2015196038 A | 11/2015 |
| KR | 101530225 B1 | 6/2015 |
| KR | 1020150062494 A | 6/2015 |
| KR | 1020150128764 A | 11/2015 |
| KR | 1020170083186 A | 7/2017 |

* cited by examiner

SMART SHOE SYSTEM FOR CALCULATING ENERGY EXPENDITURE

RELATED APPLICATIONS

This application is a 35 U.S.C. 371 national phase filing from International Application No. PCT/KR2018/008467, filed Jul. 26, 2018, which claims priority to Korean Application No. 10-2017-0096800, filed Jul. 31, 2017, the contents of which are incorporated herein by reference.

Technical Field

The present disclosure relates to a smart shoes system for calculating energy expenditure, and more specifically, to a smart shoes system for calculating energy expenditure using a sensor for measuring pressure.

Background Art

Thanks to the development of electronic technologies, various types of electronic devices are used in various fields. Particularly, the health care industry is growing with the development of information and communication technology. The health care industry is an overall healthcare business, and is a concept which collectively refers to not only typical simple treatment services, but also disease prevention, management, remote examination, and visiting health consulting, and the like.

In addition, with the miniaturization and mass production of various devices and with increasing interest in health care, smart clothing and smart shoes capable of accurately checking various biological signals and health information of people in everyday life without having to visit medical institutions are being developed. Typical smart shoes are provided with an insole containing a pressure sensor, and may transmit information about a wearer's weight, center of gravity, and movement to a smart phone.

Particularly, a prior art Korean Patent Registration No. 10-2014-0039572 discloses a configuration for calculating the degree of energy expenditure by receiving a piezoelectric signal and a piezocapacitance signal and storing the same as an ambulation signal, rectifying and then integrating the piezoelectric signal, and rectifying and then integrating the slope of the piezocapacitance signal. In addition, there are various techniques presented for measuring the wearer's movement information and energy expenditure using a smart watch or a smart band.

However, techniques typically presented show a considerable accuracy for items which directly check the condition of a wearer, such as steps, travel distance and heart rate, but show a significant error for items which indirectly check the condition of the wearer, such as energy expenditure from the actual energy expenditure.

Accordingly, there is a need for a method for calculating results close to the actual energy expenditure.

DISCLOSURE OF THE INVENTION

Technical Problem

One object of the present invention is to provide a smart shoes system for calculating energy expenditure based on a stance speed which indicates the ratio of the length of smart shoes to the time which is from the moment the smart shoes touch the ground to the moment the shoes come off the ground.

Technical Solution

In order to achieve the objects, the present invention provides a smart shoes system including a plurality of sensors for sensing pressure by the sole of a wearer and transmitting the sensed pressure information to an electronic device, and an electronic device calculating the stance speed indicating the ratio of the length of the smart shoes to the time which is from the moment the smart shoes touch the ground to the moment the shoes come off the ground based on the pressure information received from the smart shoes, calculating an ambulation speed based on the calculated stance speed, and calculating energy expenditure based on the calculated ambulation speed.

Also, the electronic device may calculate the energy expenditure differently based on the ambulation speed and the weight or BMI of the wearer according to the gender of the wearer.

Also, the pressure information received from the smart shoes may be pressure information according to a plurality of steps for the wearer's left foot and right foot, and the electronic device may calculate an average maximum force, a maximum pressure, and an average pressure based on the pressure information received from the smart shoes, and calculate energy expenditure based on at least one of the average maximum force, the maximum pressure, and the average pressure and the ambulation speed, wherein the average maximum force is an average value of the maximum force of all steps for each of the left foot and the right foot, the maximum pressure is the highest of the pressures sensed by the plurality of sensors, and the average pressure is a value obtained by summing the values of the pressures sensed by the plurality of sensors and dividing the sum by the number of the plurality of sensors.

In addition, the energy expenditure may be calculated based on at least one of the average maximum force, the maximum pressure, and the average pressure, the wearer's body weight or BMI, and the ambulation speed.

In addition, the electronic device may calculate the energy expenditure differently based on the average maximum force, the maximum pressure, the average pressure, and the ambulation speed according to the gender of the wearer.

In addition, the electronic device may calculate the energy expenditure differently based on the average maximum force, the maximum pressure, the average pressure, the wearer's body weight or BMI, and ambulation speed according to the gender of the wearer.

In addition, the electronic device may calculate the ratio of each of the average maximum force, the maximum pressure, and the average pressure to the weight of the wearer, and may calculate energy expenditure based on the calculated ratio and the ambulation speed.

In addition, the electronic device may calculate the ratio of each of the average maximum force, the maximum pressure, and the average pressure to the weight of the wearer, and may calculate energy expenditure based on the calculated ratio, the wearer's body weight or BMI, and the ambulation speed.

In addition, the electronic device may calculate the energy expenditure differently based on the ratio of each of the average maximum force, the maximum pressure, and the average pressure to the wearer's body weight and the ambulation speed according to the gender of the wearer.

In addition, the electronic device may calculate the energy expenditure differently based on the ratio of each of the average maximum force, the maximum pressure, and the average pressure to the wearer's body weight, the wearer's body weight or BMI, and the ambulation speed according to the gender of the wearer.

In addition, the electronic device may calculate the ambulation speed based on at least one of age information and disease information of the wearer.

In addition, the electronic device may calculate the ambulation speed differently based on the stance speed according to the gender of the wearer.

In addition, the electronic device may calculate the ambulation speed as zero if the stance speed is zero.

In addition, the smart shoes transmit the length information of the smart shoes to the electronic device, and the electronic device may calculate the stance speed based on the difference in time between the initial point of time at which the pressure of a predetermined first sensor among the plurality of sensors was measured to the last point of time at which the pressure of a predetermined second sensor among the plurality of sensors was measured during one step.

In addition, the predetermined first sensor may be a sensor located at the end of a heel region of the smart shoes, and the predetermined second sensor may be a sensor located at the end of a toe region of the smart shoes.

In addition, the plurality of sensors may be arranged on the same plane of the smart shoes.

Advantageous Effects

According to various embodiments of the present invention described above, the smart shoe system is always worn by a wearer to measure energy expenditure in real time or measure energy expenditure for a predetermined time.

According to various embodiments of the present invention described above, the smart shoes system may calculate the ambulation speed from the stance speed and calculate the energy expenditure from the ambulation speed to calculate the energy expenditure more accurately.

BEST MODE FOR CARRYING OUT THE INVENTION

Figure 1:
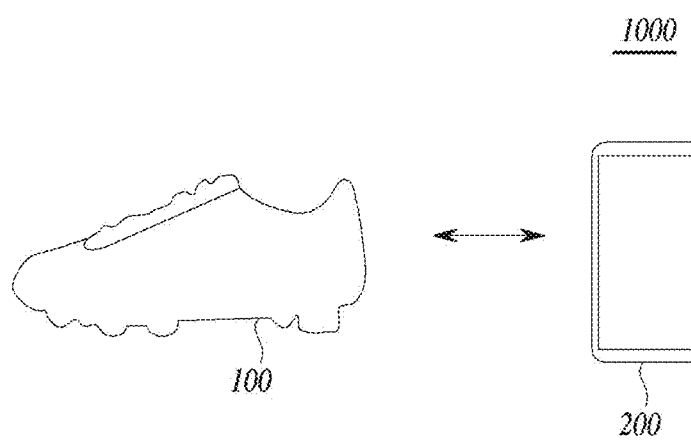
FIG. 1 is a view for explaining a smart shoes system according to an embodiment of the present invention.

Hereinafter, the present invention will be described in detail with reference to the contents described in accompanying drawings. However, the present invention is not limited or restricted to exemplary embodiments. Like reference numeral shown in each drawing denote members performing substantially the same function.

Objects and effects of the present invention may be naturally understood or more apparent by the description below. However, the objects and effects of the present invention are not limited to the following description. In addition, in describing the present invention, when it is determined that detailed descriptions of known technologies related to the present invention may unnecessarily obscure the gist of the present invention, the detailed descriptions will be omitted.

FIG. 1 is a view for explaining a smart shoes system 1000 according to an embodiment of the present invention. The smart shoes system 1000 includes smart shoes 100 and an electronic device 200.

The smart shoes 100 include a plurality of sensors for sensing the pressure applied by the soles of a wearer and may transmit sensed pressure information to the electronic device 200. For example, the smart shoes 100 may sense the pressure on each of the left sole and the right sole. In addition, the smart shoes 100 may sense the pressure on a plurality of regions such as the pressure on a toe portion and the pressure on a heel portion with respect to any one sole of the left sole and the right sole.

The smart shoes 100 may transmit information sensed by the plurality of sensors to the electronic device 200. For example, the smart shoes 100 may transmit information sensed by the plurality of sensors to the electronic device 200 in real time.

Alternatively, the smart shoes 100 may transmit information sensed by the plurality of sensors to the electronic device 200 at predetermined time intervals. In this case, the smart shoes 100 may store sensed information before transmitting the information to the electronic device 200.

Here, the sensed information may include sensed pressure information of each of the plurality of sensors, time information, arrangement information of the plurality of sensors, and the like.

The electronic device 200 according to various embodiments of the present invention is an apparatus configured to perform an operation and may be a tablet, a personal computer (PC), a personal digital assistant (PDA), a smart phone, a mobile phone, and the like.

The electronic device 200 may calculate a stance speed based on pressure information received from the smart shoes 100, the stance speed indicating the ratio of the length of the smart shoes 100 to the time which is from the moment the smart shoes 100 touch the ground to the moment the shoes 100 come off the ground, calculate an ambulation speed based on the calculated stance speed, and calculate energy expenditure based on the calculated ambulation speed.

The ambulation speed may be calculated using the stance speed of a wearer of the smart shoe system, and the value may vary depending on the ambulation state of the wearer.

Hereinafter, the structure and operation of the smart shoes 100 and a method for calculating the energy expenditure of the electronic device 200 will be described in detail with reference to the drawings.

Figure 2:
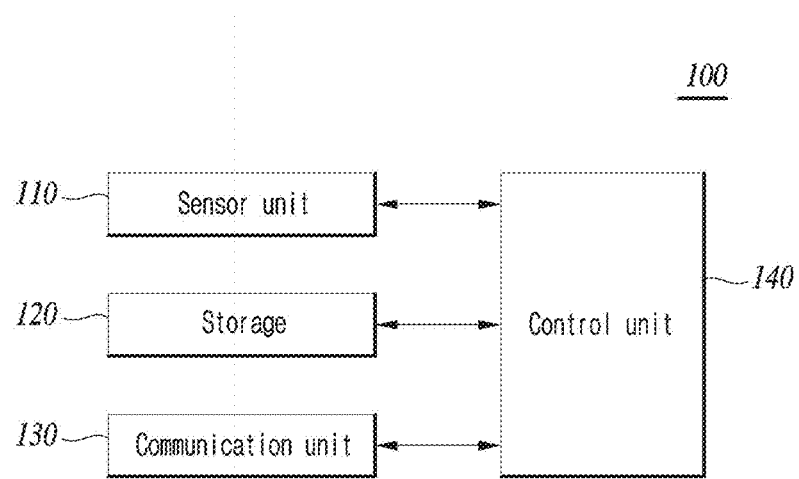
FIG. 2 is a block diagram for explaining a smart shoes system according to an embodiment of the inventive concept.

FIG. 2 is a block diagram for explaining the smart shoes system 100 according to an embodiment of the inventive concept. According to FIG. 2, the smart shoes 100 may include a sensor unit 110, a storage 120, a communication unit 130, and a control unit 140.

The sensor unit 110 may include a plurality of sensors. The sensor unit 110 will be described in detail with reference to FIG. 3A and FIG. 3B.

Figure 3A:
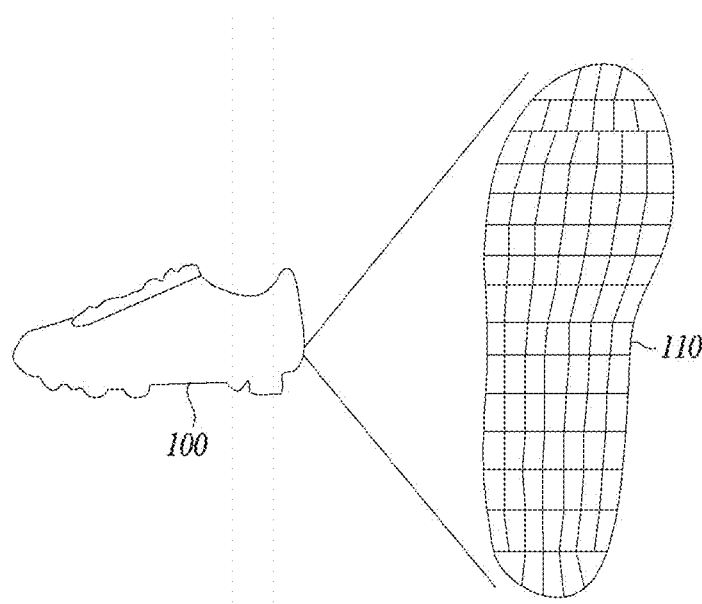
FIG. 3A and FIG. 3B are views showing a sensor unit according to an embodiment of the present invention.
Figure 3B:
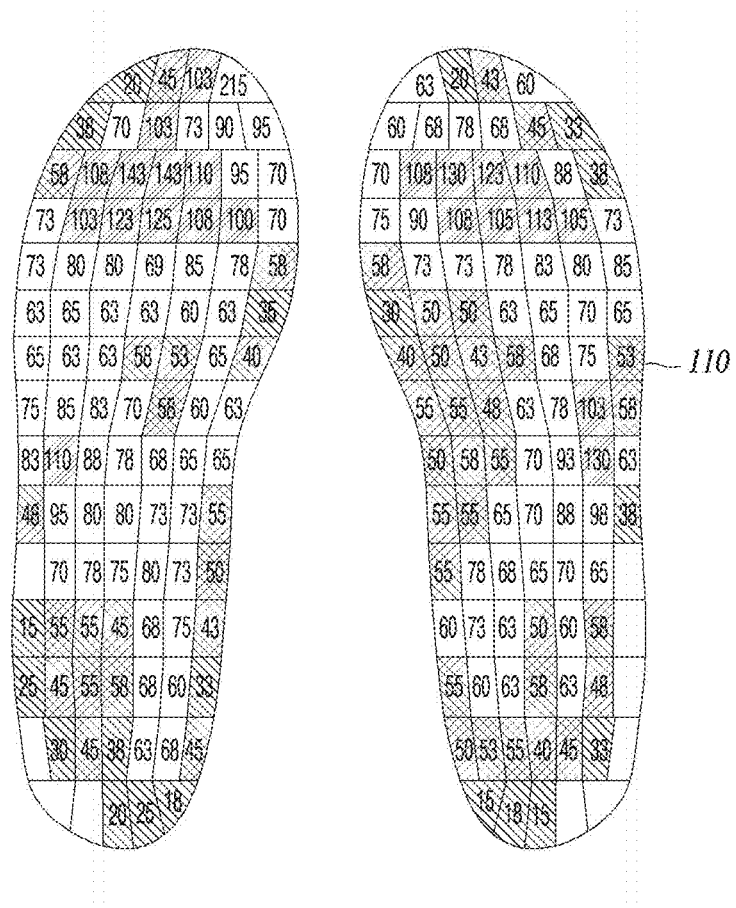

FIG. 3A and FIG. 3B are views showing the sensor unit 110 according to an embodiment of the inventive concept. First, as shown on the right side of FIG. 3A, the smart shoes 100 may form a sole portion with the sensor unit 110. The sensor unit 110 formed on the sole portion may include a plurality of sensors. For example, the plurality of sensors may be disposed on the same plane as a sole of the smart shoes 100.

In FIG. 3A, the entire region of the sole is illustrated as being provided with the plurality of sensors. However, this is only an exemplary embodiment. For example, there may be 5 sensors, and the five sensors may be disposed only on important portions such as toes and heels.

In addition, although FIG. 3A illustrates a plurality of sensors for the left foot, there may be a plurality of sensors symmetrically disposed on the right foot.

The plurality of sensors may sense pressure applied by the soles of a wearer. The pressure may be different for each detailed region of the soles of the wearer, and the results sensed by the plurality of sensors may be all different.

FIG. 3B is an example of a result of sensing the pressure applied by the soles of the wearer. The higher the pressure, the larger the value, and it can be seen that the pressure on some edges was not sensed.

The storage 120 may store information sensed by the sensor unit 100. For example, the storage 120 may store the sensed information until the information sensed by the sensor unit 100 is transmitted to the electronic device 200.

The storage 120 may be implemented in various forms such as a RAM, a ROM, and the like, and is not limited as long as it is configured to store sensed information.

The communication unit 130 is configured to perform communication with various types of external devices according to various types of communication methods. The communication unit 130 may include a Wi-Fi chip, a Bluetooth chip, a wireless communication chip, an NFC chip, and the like. The control unit 140 may transmit the sensed information to the electronic device 200 through the communication unit 130.

The Wi-Fi chip and the Bluetooth chip respectively perform communication by a Wi-Fi method and a Bluetooth method. When a Wi-Fi chip or a Bluetooth chip is used, various connection information such as an SSID and a session key may be transmitted and received first, and communication connection may be achieved using the same to transmit and receive various information. The wireless communication chip refers to a chip performing communication according to various communication standards such as IEEE, zigbee, 3rd Generation (3G), 3rd Generation Partnership Project (3GPP), Long Term Evolution (LTE), and the like. The NFC chip refers to a chip operating in an NFC (Near Field Communication) manner which uses 13.56 MHz band among various RF-ID frequency bands such as 135 kHz, 13.56 MHz, 433 MHz, 860-960 MHz, and 2.45 Ghz.

Meanwhile, the communication unit 130 may perform unidirectional or bidirectional communication with the electronic device 200. When performing unidirectional communication, the communication unit 130 may transmit a signal to the electronic device 200. When performing bidirectional communication, the communication unit 130 may receive a signal from the electronic device 200 or may transmit a signal to the electronic device 200.

The control unit 140 controls the overall operation of the smart shoes 100. Here, the control unit 140 may be implemented as a processor, a Micom, an application processor (AP), or the like.

The control unit 140 may store information sensed by the sensor unit 110 in the storage 120. The control unit 140 may transmit the information stored in the storage 120 to the electronic device 200 through the communication unit 130. Alternatively, the control unit 140 may transmit the information sensed by the sensor unit 110 to the electronic device 200 in real time. Here, the control unit 140 may distinguish pressure information according to a plurality of steps for the wearer's left foot and right foot and transmit the distinguished pressure information to the electronic device 200.

In addition, the controller 140 may store the magnitude of pressure sensed by each sensor and time information thereof. For example, the control unit 140 may store the pressure 50 of a first sensor and the time 12:05 AM at which the pressure was measured. The control unit 140 may transmit the magnitude of the pressure sensed by each sensor and the time information thereof to the electronic device 200.

The control unit 140 may transmit the length information of the smart shoes 100 to the electronic device 200 in addition to the sensed information. The length information of the smart shoes 100 may be stored in the storage 120 at the time of the manufacturing of the smart shoes 100. The control unit 140 may transmit the length information of the smart shoes 100 only once when the control unit 140 is interlocked with the electronic device 200 for the first time.

Hereinafter, the operation of the electronic device 200 which has received the sensed information will be described.

Figure 4:
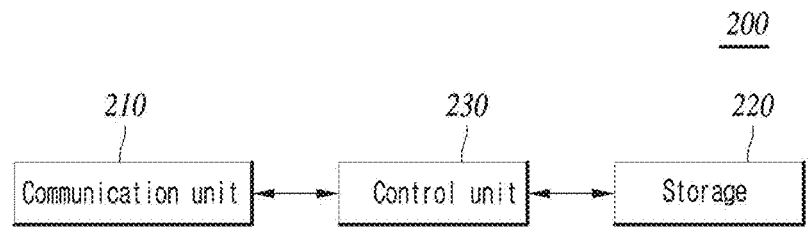
FIG. 4 is a block diagram for explaining an electronic device according to an embodiment of the present invention

FIG. 4 is a block diagram for explaining the electronic device 200 according to an embodiment of the inventive concept. According to FIG. 4, the electronic device 200 may include a communication unit 210, a storage 220, and a control unit 230.

The communication unit 210 is configured to perform communication with various types of external devices according to various types of communication methods. The communication unit 210 may include a Wi-Fi chip, a Bluetooth chip, a wireless communication chip, an NFC chip, and the like. The control unit 230 may receive the information sensed from the smart shoes 100 and the length information of the smart shoes 100 through the communication unit 210.

The Wi-Fi chip and the Bluetooth chip respectively perform communication by a Wi-Fi method and a Bluetooth method. When a Wi-Fi chip or a Bluetooth chip is used, various connection information such as an SSID and a session key may be transmitted and received first, and communication connection may be achieved using the same to transmit and receive various information. The wireless communication chip refers to a chip performing communication according to various communication standards such as IEEE, zigbee, 3rd Generation (3G), 3rd Generation Partnership Project (3GPP), Long Term Evolution (LTE), and the like. The NFC chip refers to a chip operating in an NFC (Near Field Communication) manner which uses 13.56 MHz band among various RF-ID frequency bands such as 135 kHz, 13.56 MHz, 433 MHz, 860-960 MHz, and 2.45 Ghz.

Meanwhile, the communication unit 210 may perform unidirectional or bidirectional communication with the smart shoes 100. When performing unidirectional communication, the communication unit 210 may transmit a signal to the smart shoes 100. When performing bidirectional communication, the communication unit 210 may receive a signal from the smart shoes 100 or may transmit a signal to the smart shoes 100.

The storage 220 may store pressure information received from the smart shoes 100. In addition, the storage 220 may store a method for calculating a stance speed, an ambulation speed, and energy expenditure from the received pressure information.

The storage 220 may be implemented in various forms such as a RAM, a ROM, and the like, and is not limited as long as it is configured to store received information.

The control unit 230 controls the overall operation of the electronic device 200. Here, the control unit 230 may be implemented as a processor, a Micom, an application processor (AP), or the like.

First, stance phases and swing phases will be described in order to help understand an ambulation cycle. The stance phase refers to the whole period of time during which a foot is in contact with the ground, and the swing phase refers to the period of time during which the foot is in the air to allow a body to move forward.

The control unit 230 may calculate the stance speed indicating the ratio of the length of the smart shoes 100 to the time which is from the moment the smart shoes 100 touch the ground to the moment the shoes 100 come off the ground based on the pressure information received from the smart shoes 100. That is, the stance speed means the ratio of the length of the smart shoes 100 to the stance phase.

For example, the control unit 230 may calculate the stance speed based on the difference in time between the initial point of time at which the pressure of a predetermined first sensor among the plurality of sensors of the smart shoes 100 was measured to the last point of time at which the pressure of a predetermined second sensor among the plurality of sensors of the smart shoes 100 was measured during one step.

Here, the predetermined first sensor may be a sensor located at the end of a heel region of the smart shoes 100, and the predetermined second sensor may be a sensor located at the end of a toe region of the smart shoes 100.

In addition, the control unit 230 may calculate a plurality of stance speeds for a plurality of steps in the same manner as described above, and calculate a value obtained by averaging the stance speeds as the stance speed.

Alternatively, the control unit 230 may calculate a stance speed for the step of the left foot and a stance speed for the step of the right foot in the same manner as described above, and calculate a value obtained by averaging the stance speeds as the stance speed.

The control unit 230 may calculate an ambulation speed based on the calculated stance speed. In particular, the control unit 230 may calculate the ambulation speed based on at least one of age information and disease information of the wearer.

In addition, the control unit 230 may calculate the ambulation speed differently based on the stance speed according to the wearer's gender.

However, if the stance speed is zero, the control unit 230 may calculate the ambulation speed as zero. When the stance speed is zero, the wearer may be in a stationary state, so that the control unit 230 may calculate the ambulation speed as zero.

Meanwhile, the wearer's age information, disease information, and the like may be input by the wearer through the electronic device 200 or already stored.

The control unit 230 may calculate an energy expenditure based on the calculated stance speed.

Particularly, the control unit 230 may calculate the energy expenditure differently based on the ambulation speed and the weight or BMI of the wearer according to the gender of the wearer.

The weight of the wearer may be measured using a scale, and the unit of the weight is N or kg.

The body mass index (BMI) is calculated from the relation between height-stature, the appearance of the entire body, and since it is highly relevant to the body mass status, the BMI is a globally and widely used as a measure of 'obesity' and health, and thus, is used as a major research index. The BMI may be calculated by 'Body Mass Index (BMI)=square (m) of weight/stature.'

Meanwhile, the wearer's weight, BMI, gender information, or the like may be input by the wearer through the electronic device 200 or already stored.

Meanwhile, the control unit 230 may further use an additional indicator (for example, weight or BMI) to improve the accuracy of the calculation of the energy expenditure.

First, the electronic device 200 may receive pressure information according to a plurality of steps for the left foot and the right foot of the wearer from the smart shoes 100. The control unit 230 may calculate the average maximum force, the maximum pressure, and the average pressure based on the pressure information received from the smart shoes 100, and calculate energy expenditure based on at least one of the average maximum force, the maximum pressure, and the average pressure and the ambulation speed.

Here, the average maximum force is the average value of the maximum force of all steps for each of the left foot and the right foot, the maximum pressure is the highest of the pressures sensed by the plurality of sensors, and the average pressure is a value obtained by summing the values of the pressures sensed by the plurality of sensors and dividing the sum by the number of the plurality of sensors.

In addition, the control unit 230 may calculate energy expenditure based on at least one of the average maximum force, the maximum pressure, and the average pressure, the wearer's body weight or BMI, and the ambulation speed.

Also, the control unit 230 may classify a wearer based on the gender information of the wearer, and may calculate energy expenditure based on at least one of the average maximum force, the maximum pressure, and the average pressure and the ambulation speed.

In particular, the control unit 230 may calculate the energy expenditure differently based on the average maximum force, the maximum pressure, the average pressure, and the ambulation speed according to the gender of the wearer.

In addition, the control unit 230 may calculate the energy expenditure differently based on the average maximum force, the maximum pressure, the average pressure, the wearer's body weight or BMI, and ambulation speed according to the gender of the wearer.

Meanwhile, the wearer's gender information and the like may be input by the wearer through the electronic device 200 or already stored.

In addition, the control unit 230 may calculate the ratio of each of the average maximum force, the maximum pressure, and the average pressure to the wearer's body weight, and may calculate energy expenditure based on the calculated ratio and the ambulation speed. Here, the wearer's body weight may be calculated based on the received pressure information. Alternatively, the wearer may input the body weight of the wearer through the electronic device 200.

Furthermore, the control unit 230 may calculate the ratio of each of the average maximum force, the maximum pressure, and the average pressure to the weight of the wearer, and calculate energy expenditure based on the calculated ratio, the wearer's body weight or BMI, and the ambulation speed.

Here, the control unit 230 may change the unit of the average maximum force from N to Kgf to calculate the ratio of the average maximum force to the wearer's body weight. Also, the control unit 230 may change the unit of body weight from Kgf to kPa to calculate the ratio of each of the maximum pressure and the average pressure to the wearer's body weight.

Furthermore, the control unit 230 may classify a wearer based on the gender information of the wearer, and calculate the energy expenditure based on the calculated ratio and the ambulation speed.

In particular, the control unit 230 may calculate the energy expenditure differently based on the ratio of each of the average maximum force, the maximum pressure, and the average pressure to the wearer's body weight and the ambulation speed according to the gender of the wearer.

In addition, the control unit 230 may calculate the energy expenditure differently based on the ratio of each of the average maximum force, the maximum pressure, and the average pressure to the wearer's body weight, the wearer's body weight or BMI, and the ambulation speed according to the gender of the wearer.

Meanwhile, the wearer's gender information and the like may be input by the wearer through the electronic device 200 or already stored.

Meanwhile, in the above description, it was described that the electronic device 200 calculates the average maximum force, the maximum pressure, and the average pressure. However, the embodiment of the inventive concept is not limited thereto. For example, the control unit 140 of the smart shoes 100 may calculate the average maximum force, the maximum pressure, and the average pressure from the sensed pressure information, and transmit the calculated information to the electronic device 200.

Meanwhile, although not shown in FIG. 4, the electronic device 200 may further include a display. The display is configured to display an image processed by the control unit 230. For example, the display may display the wearer's stance speed, ambulation speed, energy expenditure, and the like.

The display may be implemented as a cathode ray tube (CRT), a liquid crystal display (LCD), a light emitting diode (LED), a plasma display panel (PDP), or the like, but is not limited thereto. Also, the display may be implemented as a flexible display, a transparent display, or the like in some cases.

Alternatively, the electronic device 200 may be provided with a speaker and provide information on the wearer's stance speed, ambulation speed, energy expenditure, and the like to the wearer as sound.

Meanwhile, in the above description, it was described that the smart shoes 100 sense pressure information and the like, and the electronic device 200 receives the same and calculates the stance speed, ambulation speed, energy expenditure, and the like, but the present invention is not limited thereto. For example, the smart shoes 100 may sense pressure information and the like, and calculate the stance speed, ambulation speed, energy expenditure, and the like by itself. In this case, the storage 120 of the smart shoes 100 may store a method for calculating stance speed, ambulation speed, and energy expenditure from the sensed pressure information.

In addition, the smart shoes 100 may be provided with at least one of a speaker and a display and directly provide the calculated stance speed, ambulation speed, and energy expenditure to the wearer.

According to various embodiments of the present invention described above, the smart shoe system is always worn by a wearer to measure energy expenditure in real time or measure energy expenditure for a predetermined time. In addition, the smart shoes system may calculate the ambulation speed from the stance speed and calculate the energy expenditure from the ambulation speed to calculate the energy expenditure more accurately.

The invention claimed is:

1. A smart shoes system comprising:
a pair of smart shoes designed to be worn on a user's left foot and right foot, each of the smart shoe including:
a sensor unit;
a storage;
a communication unit; and
a control unit operatively coupled to the sensor unit, the storage and the communication unit, wherein the sensor unit is located in a sole of the smart shoe and the sensor unit comprises a plurality of sensors located at various positions along the sole of the smart shoe, wherein each of the plurality of sensors senses a pressure exerted on a respective sensor by the user's foot when the user is wearing the smart shoe;
wherein the storage stores the pressures sensed by the sensor unit,
wherein the control unit commands the communication unit to either retrieve the pressures stored by the storage and transmit the stored pressures wirelessly or the control unit commands the communication unit to transmit the pressures sensed by the sensor unit wirelessly in real-time;
an electronic device located remotely from the smart shoe, the electronic device programmed to receive information transmitted wirelessly by the communication unit of the smart shoe, wherein the electronic device is programmed to calculate the following:
a stance speed based on pressure information sensed by the sensor unit and length information of the smart shoe, wherein the stance speed is a ratio of a length of the smart shoe to a time period representing a moment the smart shoe touches a ground to a moment the smart shoe comes off the ground;
an ambulation speed based on the calculated stance speed, wherein the ambulation speed calculated according to an ambulation state;
an average maximum force, a maximum pressure, and an average pressure based on the pressure information sensed by the sensor unit and transmitted to the electronic device, wherein the pressure information sensed by the sensor unit is pressure obtained by a plurality of steps for the user's left foot and right foot, and wherein the average maximum force is an average value of the maximum force of all steps taken by the user wearing the smart shoe, the maximum pressure is a largest of pressures sensed by the sensor unit and the average pressure is a value obtained by summing the values of pressures sensed by the sensor unit and divided by the number of the plurality of sensors;
a ratio of the average maximum force to a wearer's body weight, a ratio of the maximum pressure to the wearer's body weight, and a ratio of the average pressure to the wearer's body weight; and
energy expenditure based on the ratios of the average maximum force, the maximum pressure, and the average pressure and the calculated ambulation speed according to the ambulation state.

2. The system of claim 1 wherein the electronic device receives information concerning the user's body weight, the user's Body Mass Index (BMI) and the user's gender.

3. The smart shoes system according to claim 2, wherein the electronic device calculates the energy expenditure using the ambulation speed, the ratios of the average maximum force, the maximum pressure, and the average pressure, the ambulation state and the user's body weight or BMI according to the gender of the user.

4. The smart shoes system according to claim 2, wherein the electronic device calculates the ambulation speed using age information and disease information of the user.

5. The smart shoes system according to claim 1, wherein the smart shoes transmit the length information of the smart shoe to the electronic device, and the electronic device calculates the stance speed based on a difference in time between an initial point of time at which a pressure of a predetermined first sensor among the plurality of sensors was measured to a last point of time at which a pressure of a predetermined second sensor among the plurality of sensors was measured during one step.

6. The smart shoes system according to claim 5, wherein the predetermined first sensor is a sensor located at an end of a heel region of the smart shoes, and the predetermined second sensor is a sensor located at an end of a toe region of the smart shoes.

7. The smart shoes system according to claim 1, wherein the plurality of sensors are arranged on a same plane of the smart shoe.

* * * * *